US012068075B2

(12) United States Patent
Horton et al.

(10) Patent No.: US 12,068,075 B2
(45) Date of Patent: Aug. 20, 2024

(54) METHOD FOR INITIATING A DATA TRANSFER FROM AN IMPLANTABLE MEDICAL DEVICE

(71) Applicant: BIOTRONIK SE & Co. KG, Berlin (DE)

(72) Inventors: James Horton, Portland, OR (US); Hans-Juergen Wildau, Berlin (DE); Juergen Koeppel, Parsdorf (DE); Uwe Kamenz, Berlin (DE); Thomas Trenz, Berlin (DE); Enrico Stephan, Berlin (DE); Thomas Spiller, Berlin (DE); Thorsten Wenzlaff, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 630 days.

(21) Appl. No.: 17/284,254

(22) PCT Filed: Sep. 23, 2019

(86) PCT No.: PCT/EP2019/075486
§ 371 (c)(1),
(2) Date: Apr. 9, 2021

(87) PCT Pub. No.: WO2020/083585
PCT Pub. Date: Apr. 30, 2020

(65) Prior Publication Data
US 2021/0383922 A1 Dec. 9, 2021

Related U.S. Application Data

(60) Provisional application No. 62/750,833, filed on Oct. 26, 2018.

(30) Foreign Application Priority Data

Mar. 7, 2019 (DE) .................... 10 2019 105 801.5

(51) Int. Cl.
*A61N 1/37* (2006.01)
*A61N 1/372* (2006.01)
(Continued)

(52) U.S. Cl.
CPC ......... *G16H 40/67* (2018.01); *A61N 1/37252* (2013.01); *G16H 40/63* (2018.01)

(58) Field of Classification Search
CPC ..... A61N 1/37252; G16H 40/63; G16H 40/67
See application file for complete search history.

(56) References Cited

U.S. PATENT DOCUMENTS

| 7,369,897 B2 | 5/2008 | Boveja et al. |
| 2001/0023360 A1 | 9/2001 | Nelson et al. |
| 2010/0292556 A1 | 11/2010 | Golden |

(Continued)

FOREIGN PATENT DOCUMENTS

| CN | 103415852 A | 11/2013 |
| CN | 104683474 A | 6/2015 |
| JP | 20080521576 A | 6/2008 |
| JP | 2016122426 A | 7/2016 |

OTHER PUBLICATIONS

Chinese Office Action for Chinese Applicaiton No. 201980070654.2 dated Jun. 15, 2023 (together with English Translation).

(Continued)

*Primary Examiner* — Amanda K Hulbert
(74) *Attorney, Agent, or Firm* — Buchanan Ingersoll & Rooney PC

(57) ABSTRACT

In a method for initiating a data transfer from an implantable medical device a relay data request is generated at a remote device, the relay data request containing an implant interrogation request representing a request for the implantable medical device to create an interrogation data set. The relay data request is transferred to a patient device, and a communication link between the patient device and the implant- (Continued)

able medical device is established to transmit said implant interrogation request to the implantable medical device. An implant interrogation response is transferred from the implantable medical device to the patient device, the implant interrogation response representing a response from the implantable medical device containing said interrogation data set. The implant interrogation response is transferred from the patient device to the remote device.

14 Claims, 3 Drawing Sheets

(51) Int. Cl.
  G16H 40/63 (2018.01)
  G16H 40/67 (2018.01)

(56) References Cited

U.S. PATENT DOCUMENTS

| 2015/0065047 | A1 | 3/2015 | Wu et al. |
| 2016/0331980 | A1 | 11/2016 | Strommer et al. |
| 2017/0259072 | A1* | 9/2017 | Newham ............ A61N 1/37276 |

OTHER PUBLICATIONS

International Search Report (PCT/ISA/210) and Written Opinion (PCT/ISA/237) mailed on Jan. 2, 2020, by the European Patent Office as the International Searching Authority for International Application No. PCT/EP2019/075486.

Office Action for Japanese Patent Application No. 2021-522493 dated Jul. 28, 2023 (with English translation).

Office Action for Japanese Patent Application No. 2021-522493 dated Feb. 1, 2024 (with English translation).

* cited by examiner

METHOD FOR INITIATING A DATA TRANSFER FROM AN IMPLANTABLE MEDICAL DEVICE

CROSS-REFERENCE TO RELATED APPLICATIONS

This application is the United States national phase under 35 U.S.C. § 371 of PCT International Patent Application No. PCT/EP2019/075486, filed on Sep. 23, 2019, which claims the benefit of German Patent Application No. 10 2019 105 801.5, filed on Mar. 7, 2019 and U.S. Application No. 62/750,833, filed on Oct. 26, 2018, the disclosures of which are hereby incorporated by reference herein in their entireties.

TECHNICAL FIELD

The present invention relates to a method for initiating a data transfer from an implantable medical device and to a system for initiating a data transfer from an implantable medical device.

BACKGROUND

Implantable medical devices as known in the art can be coupled with various external devices to exchange data. For example, an implantable medical device can be coupled with a programming device that allows a clinician to adjust the implantable medical device's settings. For the coupling a magnetic switch can for example be used, which is placed over the implantable medical device. The magnetic switch has a permanent magnet whose magnetic field is detected by the implantable medical device and puts it into a coupling state in which the implantable medical device is coupled to the programming device.

In addition, in a wireless monitoring system, a patient device—also denoted as patient transceiver—is known to connect wirelessly to an implantable medical device when located near the implantable medical device. Such patient devices are used, for example, to download patient data at regular intervals (e.g. daily) from the implantable medical device and forward it to a service center. At the service center, the data is pre-processed and, if necessary, transferred to a user, e.g. a specialized clinician.

A patient device may, for example, be equipped with a wake-up function to switch an associated implantable medical device from a resting state to an active state in order to establish a communication link with the implantable medical device. The patient device for example emits a wake-up signal in a radio frequency (RF) range, which is received by the implantable medical device, whereupon it is activated for data communication with the patient device.

A potential disadvantage of a general wake-up functionality to wake up an implantable medical device is that unwanted access to the implantable medical device can potentially be gained by third-party devices that implement the patient device's communication scheme and methodology. Especially in the field of implantable medical devices with vital therapy functions such as pacemakers and implantable cardioverter defibrillators, demands on cybersecurity are generally high.

Another potential disadvantage is that the implantable medical device is awakened and a communication channel is established without taking the implantable medical device battery level into account. This may have the consequence that energy resources are no longer available for high-priority therapy functions. There is a risk of using up the battery of an implantable medical device by frequently waking up the implantable medical device, e.g. deliberately through an attack by a third party, or through a software error.

In addition, systems exist providing the possibility for a patient to initiate a recording of data by the implantable medical device. If, for example, a pacemaker patient does not feel well, e.g., if the patient feels dizzy or experiences a tachycardia, the patient can trigger the recording of an ECG by the implantable medical device, e.g. by actuating a remote control. The data recorded in this way is transferred directly to a clinician or to a service center the next time data is retrieved from the implantable medical device, for example during an examination at the clinician or via an automatic query of the patient device.

Generally, processes to access real-time status data from an implantable medical device, such as, for example, an implantable pulse generator (IPG), are presently limited to interrogated data gathered during an in-clinic follow-up or, in limited examples, a report triggered by the patient. These processes lack clinician control. Although some implantable medical devices have means for triggering an interrogation when the patient is remote from a clinician, the patient generally is involved as actor able to trigger the remote interrogation, the clinician currently having limited ability to trigger the remote interrogation by himself.

In a typical workflow, as provided by some products currently available, a patient, who feels symptomatic, may wish to send a report to a clinic, or the clinic may request that the patient generate a report. In either case, the patient follows the process to initiate the patient device to trigger the interrogation. This requires either that the patient places an interrogation wand over the implanted medical device, or if available, the patient device can connect to the implanted medical device via wireless means. The implanted medical device processes the interrogation and transmits data to the patient device. The patient then triggers the patient device to transmit an interrogation message, for example, to a service center, or if available, the patient device initiates the transmission to the service center automatically.

Thus, such solutions are patient-triggered in the sense that clinicians must rely on the patient to initiate the data capture and possibly the data transmission as well, and are therefore not in control of how or when the data is captured. Further, as the clinic cannot control receipt of the information transmitted from the implant, a clinician is not necessarily able to respond to the receipt of the data at the time it is received. This leads to a non-optimal workflow regarding the clinic review of the data. Because the transmission of data triggered by the patient and the receipt and review by the clinic are disconnected from one another, potentially a liability situation may be caused, if the clinic does not respond in a timely fashion.

U.S. Pat. No. 7,369,897 discloses a method and system of remotely controlling an implanted stimulator for providing electrical pulses to nerve tissue, comprising an implantable stimulator, an interface unit, and a mobile device such as a modified PDA or cell phone.

The present disclosure is directed toward overcoming one or more of the above-mentioned problems, though not necessarily limited to embodiments that do.

SUMMARY

It is an object of the present invention to provide a method and a system for initiating a data transfer from an implantable medical device by which patient parameters recorded by the implantable medical device are made available to the clinician remote from the patient or implantable medical device.

At least this object is achieved by a method and a system comprising the features of the respective independent claims.

According to the method, for initiating a data transfer from an implantable medical device a relay data request is generated at a remote device (e.g. a user device or a service center), the relay data request containing an implant interrogation request representing a request for the implantable medical device to create an interrogation data set. The relay data request is transferred to a patient device. A communication link is established between the patient device and the implantable medical device to transmit said implant interrogation request to the implantable medical device. An implant interrogation response is transferred from the implantable medical device to the patient device, the implant interrogation response representing a response from the implantable medical device containing said interrogation data set. The implant interrogation response is transferred from the patient device to the remote device.

By means of the method, a scheme for interrogation of an implantable medical device is provided where, in one embodiment, no patient interaction is required (as long as the patient device is close enough to the implantable medical device and has connectivity (e.g. network connectivity)), allowing improving control of data capture, improving clinic workflows, and/or reducing travel demands on patients to achieve desired care.

It is to be noted that the technology described herein may also work with an implantable medical device capable of a patient-triggered interrogation.

The method allows a user, such as a clinician at a hospital, to interrogate, using a remote device, a medical device implanted in a patient. For this, a user may trigger the generation of a relay data request at a remote device, for example using a user device such as a mobile device, a laptop computer, a tablet computer, a stationary personal computer or the like, wherein the user may trigger the generation of the relay data request on the user device itself or may access, via the user device, a service center such that the relay data request is generated at the service center.

Upon generation of the relay data request at the remote device, e.g. at the user device or at the service center, the relay data request is sent to a patient device which, upon receiving the relay data request, initiates a communication with the implantable medical device such that a communication link is established between the patient device and the implantable medical device.

When generating the relay data request, the remote device also generates an implant interrogation request which is transferred to the patient device as part of the relay data request. The patient device extracts the implant interrogation request from the relay data request and forwards the implant interrogation request to the implantable medical device, which in this way is caused to collect data according to specifications included in the implant interrogation request, the collecting of data potentially including the conduction of measurements or the collection of data which has been previously obtained, e.g. from previous measurements.

Because the implant interrogation request is generated at the remote device according to specifications of a user, for example a clinician, who triggers the interrogation at the remote device, the collection of data at the implantable medical device is triggered and controlled by the user via the remote device. The implantable medical device hence, via the implant interrogation request, obtains a specified request causing the implantable medical device to collect a specific set of data to produce the interrogation data set, the interrogation data set being tailored for example to facilitate a diagnosis in view of the patient's complaints and a physical condition present at the patient.

Once the data is collected by the implantable medical device, the implantable medical device includes the data in an implant integration response and transfers the implant interrogation response to the patient device, which forwards the implant interrogation response to the remote device, such that a user is enabled to examine the data.

In one embodiment, the steps of transferring the relay data request, of establishing the communication link, of transferring the implant interrogation request and of transferring the implant interrogation response are performed by the remote device, the patient device and the implantable medical device without requiring any action by a user and/or a patient. In particular, a user, after triggering the interrogation at the remote device, has to take no further action in the context of generating the relay data request, the implant interrogation request, and the implant interrogation response. A patient, in one embodiment, for example does not have to participate in the interrogation process at all, the patient potentially not even knowing that an interrogation takes place.

For example, if a patient device is already in a position such that it is able to communicate with the medical device implanted in the patient, a real-time interrogation may take place without involvement of the patient. If the patient device at the time of receiving the relay data request is not in a position such that it is able to communicate with the medical device implanted in the patient, the establishing of the communication link and the forwarding of the implant interrogation request may be delayed until the patient device is able to communicate with the implantable medical device (for example at night), again without conscious involvement of the patient.

In one embodiment, the relay data request, in addition to the implant interrogation request, may contain at least one of a priority value, an implant wake-up token, and an implant specific key (or several implant specific keys) to be used by the patient device for communicating with the implantable medical device. The priority value herein indicates a priority of the interrogation and may for example have values of "slow", "medium", "fast", "very fast" and "real time". According to the priority value, the relay data request and the implant interrogation request are processed at the remote device, the patient device and the implantable medical device. The implant wake-up token is different for each implant interrogation request and may allow the implantable medical device to verify the authenticity of the request and the authorization of the requesting user. One or multiple keys may be used for securing the communication between the patient device and the implantable medical device (e.g. confidentiality, authenticity and/or authorization). If the patient device and/or the implantable medical device do not have the processing power necessary for asymmetric cryptography, the patient device may use the implant specific key(s) contained in the relay data request.

In one embodiment, prior to transferring the relay data request to the patient device, the remote device may transmit at least one patient device wake-up request to the patient device. By means of the patient device wake-up request the patient device is activated, and it is caused to establish a communication connection to the remote device, such that a communication between the patient device and the remote device becomes possible.

Once the communication connection is established, the remote device may transfer the relay data request to the patient device using the communication connection, such that the patient device receives the relay data request and the implant interrogation request included therein.

The patient device wake-up request may for example be sent via a wireless communication channel, for example using a mobile network. For example, the patient device wake-up request may be sent as a text message (e.g., according to the Short Messaging Service, in short SMS).

In one embodiment, the remote device may send a multiplicity of patient device wake-up requests, for example in a burst of patient device wake-up requests, in order to reduce the risk that the patient device does not receive the patient device wake-up request, in particular in case the transmission technology does not include a reliable reception feedback scheme, as it is for example the case with SMS.

The remote device may send patient device wake-up requests in a schematic order. For example, the remote device may send patient device wake-up requests in a first wake-up sequence in a repeated fashion for a first duration, for example lasting between 1 minute and 20 minutes, for example between 10 and 15 minutes. If the patient device cannot be woken up in this initial, first wake-up sequence, the transmission of patient device wake-up requests is paused, and then initiated anew after a pause with a pause duration of, for example, between 30 minutes and 2 hours. Then, patient device wake-up requests are sent in a second wake-up sequence with a second duration of, for example, between 1 and 10 minutes, for example between 5 minutes and 8 minutes. This may be repeated, until the patient device is successfully activated. After 3 days, the wake-up attempts are terminated if unsuccessful until then.

A patient device wake-up request may include a patient device wake-up token, which is different for each wake-up attempt of the patient device. The patient device wake-up token allows the patient device to determine whether it has already responded to a wake-up attempt, such that it is made sure that the patient device connects only once for each relay data request to be sent to the patient device.

In one embodiment, the communication connection established by the patient device for data communication between the remote device and the patient device is established using a wireless connection, for example a mobile network connection. For the data communication, a mobile communication protocol, for example based on a TCP protocol, may be used. By means of the communication protocol, a secure connection can be established, applying, for example, suitable encryption, authentication and/or authorization mechanisms, such that a connection is only established between a valid remote device and a valid patient device, the communication is confidential and cannot be manipulated by a third-party.

Based on the priority value included in the relay data request, the patient device may terminate other connections with the remote device and immediately establish a communication link with the implantable medical device, in particular for priority values indicating a high priority. In this way, slow operations, such as for example an ongoing firmware update, may be skipped or delayed in order to prioritize the interrogation of the implantable medical device.

Once the patient device has received a relay data request with a high priority and the implant interrogation request included therein, the patient device causes the establishing of a communication link between the patient device and the implantable medical device. For this, the patient device, for example, may transmit one or multiple implant wake-up requests to the implantable medical device, causing the implantable medical device to be activated and to establish said communication link. Via the communication link, then, the patient device forwards the implant interrogation request to the implantable medical device, upon which the implantable medical device collects data as defined in the implant interrogation request to generate said interrogation data set to be included in the implant interrogation response.

The implant wake-up request may for example be sent using a MICS (Medical Implant Communication Service), MedRadio (Medical Device Radiocommunication Service), MEDS (Medical Data Service), ISM (Industrial, Scientific and Medical) or BLE (Bluetooth Low Energy) communication. Likewise, the communication link established in response to the implant wake-up request may be a MICS, MedRadio, MEDS, ISM or BLE link. The communication link may be secured (e.g. confidentiality, authenticity and/or authorization) using the key(s) as included in the relay data request transferred from the remote device to the patient device.

For example, in one embodiment, the least interfered channel in the MICS/MedRadio/MEDS scheme may be used.

The implant wake-up request may be transmitted together with the implant wake-up token. Using the implant wake-up token, the implantable medical device may protect itself against replay attacks and also an authorization of the patient device, of the remote device and/or of the requesting user may take place during the communication with the implantable medical device. For example, the patient wake-up token may contain a token value chosen by the implantable medical device (e.g. a counter initialized by a random number and incremented after each interrogation). The token value is transmitted in a regular fashion from the implantable medical device to the remote device, for example each night during a regular reporting between the implantable medical device and the remote device. When initiating an interrogation, the remote device creates an implant wake-up token containing the token value and, for example, secures it with a key for proofing authenticity of the request and/or authorization of the requesting user. The implant wake-up token is sent to the patient device as part of the relay data request, which forwards the implant wake-up token to the implantable medical device, which verifies the validity of the transmitted wake-up token. In one embodiment, the implantable medical device will only establish a communication link with the patient device if the wake-up token is valid, which means that the transmitted token value matches the value expected by the implantable device (e.g. equality in case of a counter value) and the authenticity of the request and/or authorization of the patient device, remote device and/or requesting user can be successfully verified based on the key(s) used by the remote device and/or patient device (e.g. the token has been signed by the remote device and/or a message authentication code has been generated by the patient device that covers the token as well as the channel of the MICS/MedRadio/MEDS scheme that is used for the current communication link).

The collection of data by the implantable medical device takes place as specified in the implant interrogation request. Once the data is collected, an interrogation data set is created and included in an implant interrogation response, which is sent to the patient device and via the patient device to the remote device.

The collection of data may include measurements performed by the implantable medical device. The collection of data, in addition or alternatively, may include the assembling of data already stored in the implantable medical device, such as ongoing IEGM recordings or statistics data.

If the activity triggered by the implant interrogation request is within a time duration supported by the communication protocol, the communication link between the patient device and the implantable medical device may be maintained, and after data collection the implant integration response is sent to the patient device. If the duration of the activity of the implantable medical device is longer than supported by the communication protocol, the connection is terminated after sending the implant interrogation request and re-established after collection of the data is completed, such that after re-establishment of the communication link the implant interrogation response is forwarded to the patient device.

On reception of the implant interrogation response, in one embodiment, the patient device terminates the connection with the implantable medical device and initiates a connection to the remote device, for example using a mobile connection. The communication connection between the patient device and the remote device hence is, in one embodiment, established anew, and the implant interrogation response is forwarded to the remote device.

Analogously to the communication link between the patient device and the implantable medical device, for the forwarding of the implant interrogation response to the remote device the same communication connection as used for the sending of the relay data request from the remote device to the patient device could be used, in case the communication protocol supports a connection over a duration required for the activity of the implantable medical device in the context of the interrogation and does not interfere with the communication link between the patient device and the implantable medical device.

Upon reception of the implant interrogation response, the remote device, for example a service center, may then calculate a new patient status based on the data contained in the implant interrogation response.

If the remote device is, for example, a service center to which the user can connect using a website or the like, the remote device may notify a user such that data relating to the interrogation is available, upon which the user can connect to the remote device and can examine the data. The notification of the user may for example take place by a text message, such as an SMS message or an email.

A system for initiating a data transfer from an implantable medical device may comprise a remote device, a patient device, and an implantable medical device. The remote device is configured to generate a relay data request, the relay data request containing an implant interrogation request representing a request for the implantable medical device to create an interrogation data set. The remote device is further configured to transfer the relay data request to the patient device. The patient device and the implantable medical device are configured to cooperate to establish a communication link between the patient device and the implantable medical device to transmit said implant interrogation request to the implantable medical device. The implantable medical device is configured to transfer an implant interrogation response to the patient device, the implant interrogation response representing a response from the implantable medical device containing said interrogation data set. The patient device is configured to transfer the implant interrogation response from the patient device to the remote device.

By the above, a system and a method for real-time, remotely triggered data update from an implantable medical device may be provided. The system comprises an implantable medical device (for example an IPG), a patient device (may also be called patient transceiver), and a remote device, e.g. a service center comprising a central processing (and optionally admin) system and allowing access via a clinician user interface (e.g. a computer, a tablet or a notebook). The system is used for triggering e.g. a real-time interrogation of the current data of the patient's implantable medical device for remote analysis. The invention can be used in multiple areas of IPG medical device application, e.g. SCS, CRM, etc.

In one embodiment, a clinician-triggered request for the interrogation of the implant becomes possible, rather than patient-triggered (though this schema could also work with an implant capable of a patient-triggered interrogation). The clinician-triggered request of the interrogation may, in one embodiment, be initiated remotely from a clinician user interface, wherein data can be simultaneously viewed remotely at multiple user interfaces.

One or more (e.g. all) steps in the sequence of communications may involve a "handshake" process that ensures secure communication and provides automatic data persistence and communication repetition to ensure that the communication between each component is completed.

The method and system is intended to ensure data transmission between a patient device and an implantable medical device that is safe from attacks by third parties and that may be energy-saving for the battery of the implantable medical device.

In another, general aspect, a procedure is proposed for transferring data between an implantable medical device and a remote device, comprising the steps: (a) triggering an implant interrogation request by a user via the remote device; (b) transferring the implant interrogation request from the remote device to a patient device as part of a relay data request; (c) establishing a communication link between a patient device and a patient's implantable medical device; (d) transferring an implant interrogation response containing the interrogation data set from the implantable medical device to the patient device; and (e) transferring the implant interrogation response from the patient device to the remote device. Herein steps, (b) to (e) are performed by the remote device, the patient device and implantable medical device without requiring any action of the user or patient.

The user is, for example, a responsible clinician or trained personnel of a clinic or medical practice.

A remote device is, for example, a computer with an Internet connection or any other suitable device with sufficient processor power and a display for operation by the user. A remote device may also be a service center which may be accessed by a user using a website or the like.

The procedure allows patient parameters recorded by the implantable medical device to be made available immediately after recording to a user remote from the patient or implantable medical device where the implant interrogation request is initiated by the user. The entire procedure may, in one embodiment, take place during a session, i.e. from start to finish the user can be in contact or interaction with the remote device. For example, an animated graphic on a screen of the remote device can visualize the progress of the process, e.g. by means of a progress bar or similar.

From the time the user triggers the implant interrogation request until the implant interrogation response is received at the remote device, in one embodiment no input by the user or patient is required. All data transfer steps are performed automatically by the remote device, patient device or implantable medical device. This prevents delays, e.g. due to further input or confirmation steps by users or patients.

In one embodiment, step (b) involves transferring the implant interrogation request as part of the relay data request from a user device to a patient device via a service center. Alternatively or additionally, step (d) may include transferring the implant interrogation response from the patient device to a user device via a service center. The request and/or the response is pre-processed and/or stored by the service center.

Optionally, according to one aspect, step (a) has a preceding step in which the patient contacts the user.

For example, if a patient experiences abnormalities (e.g. dizziness or tachycardia if the implantable medical device is a pacemaker), the patient can contact a user. For this purpose, the patient can call the user, write a short message or activate a function on the patient device. In direct contact with the user, the patient expresses his/her complaints, whereupon the user initiates appropriate measures. If the complaints are alarming, the user can, for example, notify the medical emergency service directly. In the case of inconspicuous complaints, the user could reassure the patient without taking any action. According to the invention, in all other cases the user can request a data transfer from the patient's implantable medical device via the procedure according to the invention and call it up on the remote device within a short time. In this way, in a situation where the patient feels anomalies, there is direct contact with the user. The user retrieves implantable medical device data directly so that all information related to the situation is available to the user. In addition, through direct contact, the user can instruct the patient to stay in range of the patient device and provide psychological assistance to the patient.

Further, according to an embodiment, step (c) comprises that the patient device sends at least one implant wake-up request to the implantable medical device, and the implantable medical device provides a time window for receiving said request at regular intervals. In this way, the implantable medical device 'listens' within the time window to see if there is an implant wake-up request from a patient device.

According to aspects of the present invention, the interval is anywhere between 10 s to 10 minutes, and/or the time window has a duration of 0.1 ms to 5 ms. For example, the interval is 10 s, 20 s, 30 s, 40 s, 50 s, 1 minute, 1.5 minutes, 2 minutes, 3 minutes, 4 minutes, 5 minutes, 6 minutes, 7 minutes, 8 minutes, 9 minutes or 10 minutes and/or the time window has a duration of 0.5 ms or 1 ms. The length of interval and the duration of the time window must be chosen so that an implant wake-up request is received by the implantable medical device within a reasonable period of time so that the total duration of the procedure according to the invention remains within acceptable limits for users and patients and the battery of the implantable medical device does not get drained too much.

According to one aspect, the communication link between patient device and implantable medical device is established by the implantable medical device when the implant wake-up request is received within the time window. According to one embodiment, the implantable medical device may refuse or delay establishing a communication link. By refusing or delaying a communication link, it can be achieved that the implantable medical device can decide whether a communication link is suitable, e.g. depending on its battery status or the prioritization of device functions. If, for example, the battery level is low and/or other implant functions are given higher priority (e.g. therapy functions), the implantable medical device may decide not to establish a communication link or may postpone the establishing of the communication link. In this way, the energy management of the implantable medical device can be controlled by the implantable medical device itself.

According to one aspect, upon reception of an implant interrogation request, the implantable medical device performs a measurement of new data, the new data relating to at least one patient parameter, an implant parameter, or another parameter. The new data obtained in the measurement may be added to the implant interrogation response to be transferred to the patient device. In this way, the user receives the currently measured data of a patient parameter, an implant parameter, and/or another parameter. The user, in one embodiment, can select the parameter for which the measurement of new data is to be carried out beforehand. This allows the user to select a parameter that potentially relates to complaints expressed by a patient. If a heart patient with a pacemaker or implantable cardioverter defibrillator complains of tachycardia, the user can choose, for example, to have an electrocardiogram (ECG) re-measured.

An implant interrogation response, in one embodiment, includes at least the data of the following parameters or a combination of these: a patient parameter, a technical implant parameter, or another parameter.

The patient parameter, in one embodiment, may comprise at least one of an electrocardiogram, an impedance cardiogram, electroencephalogram (EEG), activity data, pressure readings, biochemical or other sensory data, statistics or overviews of recorded measurement data and/or therapy delivery and/or therapy efficiency, stored patient and personal data.

The implant parameter, in one embodiment, may comprise at least one of battery voltages, electrode impedances, signal amplitudes, data transmission statistics, statistics on special device states such as battery exhaustion or backup mode, current programming settings of the implantable medical device.

The other parameter, in one embodiment, may include at least one of further data from information units captured by the implantable medical device, such as external sensors and wearables, data on diagnostic or therapeutic procedures that have taken place, such as automatically detected MRI examinations, other information brought about by the patient, such as a voice message recorded by the implantable medical device.

According to one aspect, at least one transmission/reception/sending of data and/or communications is wireless. Network systems for remote communication such as fixed telephone networks or mobile radio networks can be used to transmit the request from a user device directly to the patient device or from a user device via a service center to a patient device. Communication and data exchange between the patient device and the implantable medical device can be performed using the Medical Implant Communication Service (MICS), MedRadio (Medical Device Radiocommunication Service), MEDS (Medical Data Service), Industrial, Scientific and Medical (ISM) or Bluetooth Low Energy (BLE) frequency bands. The MICS/MedRadio/MEDS and ISM bands are advantageous because they are special frequency bands dedicated to medical data transmissions, so that few interfering signals interfere with communication.

Furthermore, according to other aspects, the execution of steps (a) to (e), i.e. from triggering the implant interrogation request until the implant interrogation response is available to the user on the remote device, must remain within an acceptable time frame of a session between user and patient, with a maximum of 5 to 15 minutes based on the experiences of users and patients not exceeding such time frame.

It is conceivable that steps (a) to (e) could be executed via a remote device for more than one implantable medical device, according to further forms of the invention. In this way, a user can trigger multiple requests to transfer data for multiple implantable medical devices to optimize time management in the clinic or doctor's office through parallel processes.

According to aspects, a system comprising a remote device, a patient device and an implantable medical device is proposed to perform the procedure according to the invention.

According to one embodiment, the average current consumption of the implantable medical device shall be a maximum of 0.1 µA, 0.5 µA, 1 µA, 2 µA, 3 µA, 4 µA, 5 µA or 10 µA when using a 3V battery by providing and performing the functions to enable the procedure according to the invention. The average current consumption shall not remarkably shorten the device lifetime Alternatively or additionally, the device runtime of the implantable medical device shall be shortened by a maximum of 1%, 2%, 5%, or 10% of the total device runtime by providing and performing the functions to enable the inventive process.

Alternatively or in addition, the device life of the implantable medical device shall be shortened by a maximum of 1, 2, 3 or 6 months in relation to an expected total device life of 10 years by providing and performing the functions to enable the procedure according to the invention.

By means of the method and system as described herein, an implantable medical device may be operated at acceptable energy costs in relation to the total running time of the device battery, while offering an improved way of interrogation by a clinician with no or at least reduced patient interaction.

The implantable medical device may for example be a pacemaker, an implantable cardioverter defibrillator, a Cardiac Resynchronization Therapy (CRT) device, a brain pacemaker, a spinal cord stimulator, a cardiac monitoring device without therapy function, or any other type of implantable device with a function to record a patient parameter.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The concept of the present invention shall subsequently be described in more detail with reference to the embodiments shown in the figures. Herein.

DETAILED DESCRIPTION

Figure 1:
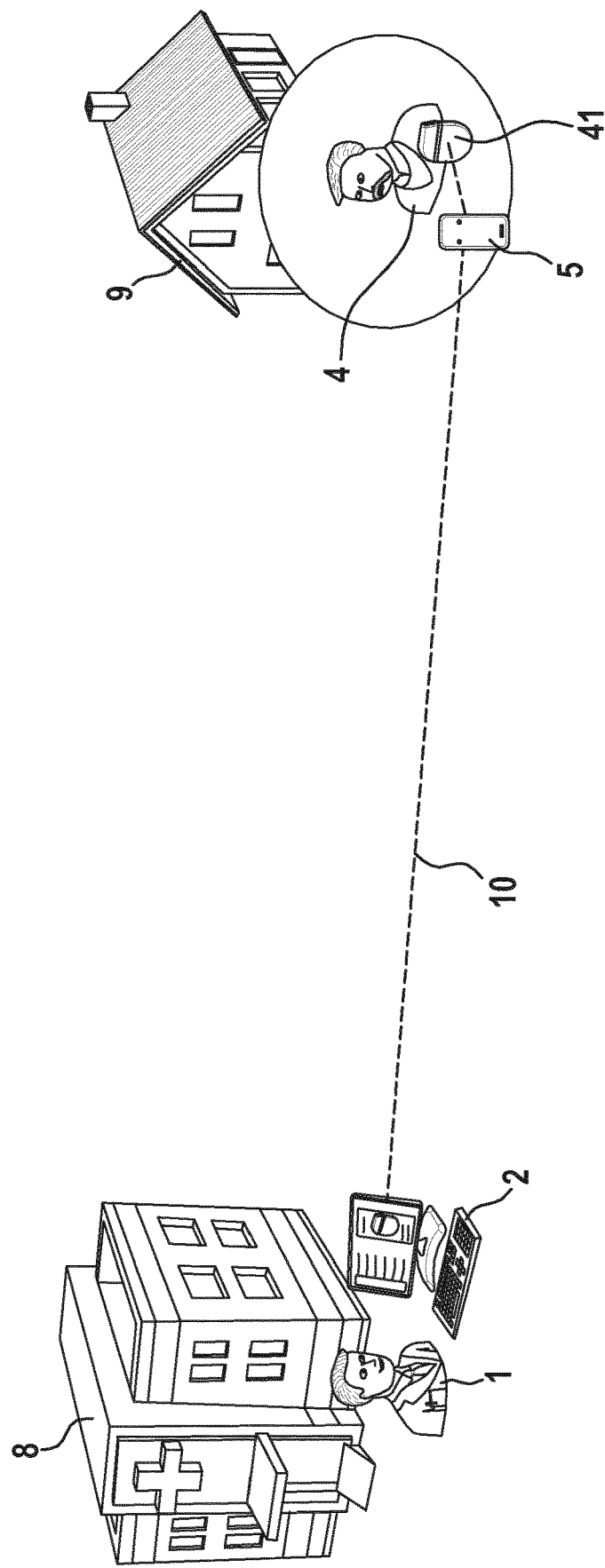
FIG. 1 shows a schematic drawing of an embodiment of a system for transferring data from an implantable medical device (IMD) directly to a user device.

FIG. 1 schematically shows an embodiment of a system for transferring data from an implantable medical device 41 to a remote device in the shape of a user device 2.

In the embodiment of FIG. 1, within a general setup a user 1, for example a clinician at a hospital 8, triggers an implant interrogation request for an implantable medical device 41 via its user device 2. In response to the trigger, a wireless connection 10 to a patient device 5 is established. A communication connection is established between the patient device 5 and a patient's 4 implantable medical device 41, and the implant interrogation request is first transferred from the user device 2 to the patient device 5 and then from the patient device 5 to the implantable medical device 41. In response to the implant interrogation request, an implant interrogation response is first transferred from the implantable medical device 41 to the patient device 5 and then from the patient device 5 to the user device 2. For example, the user 1 is a cardiologist of a hospital 8, while the patient 4 is in its home 9.

The patient 4 may have previously made contact with the user 1 and may have informed the user 1 of any complaints, for example by telephone. Alternatively, the patient 4 has made no previous contact to the user 1, and potentially is not even aware of a data exchange between the user device 2, the patient device 5 and the implantable medical device 41.

Figure 2:
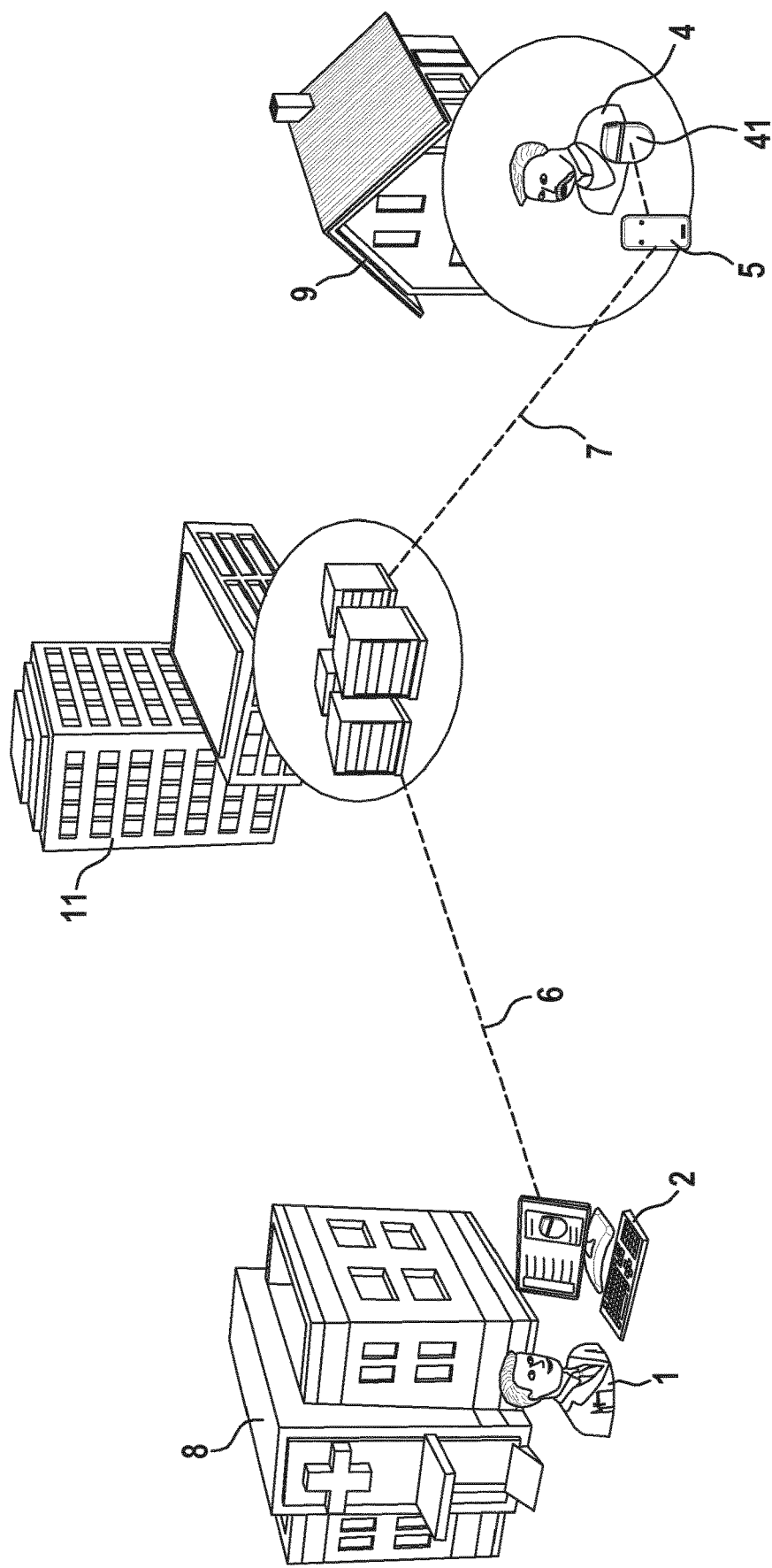
FIG. 2 shows a schematic drawing of another embodiment of a system for transferring data from an implantable medical device (IMD) to a user device via a service center.

FIG. 2 schematically shows another embodiment of a system for transferring data from an implantable medical device 41 to a user device 2 via a service center 11. The system of FIG. 2 differs from the system of FIG. 1 in that the user 1 by means of the user device 2 accesses a service center 11, for example by establishing a connection 6 the service center 11 for triggering an implant interrogation request via the user device 2. Accordingly, an implant interrogation request is generated and is transmitted by the service center 11 to the patient unit 5 via a wireless connection 7. The implant interrogation response sent from the implantable medical device 41 to the patient device 5 is then transmitted back to the service center 11 and can be forwarded by the service center 11 to the user device 2, or can be viewed by the user 1 via the user device 2 at the service center 11, for example using a website or the like. The external service center 11 can pre-process and/or store both the request information and the data packet.

Figure 3:
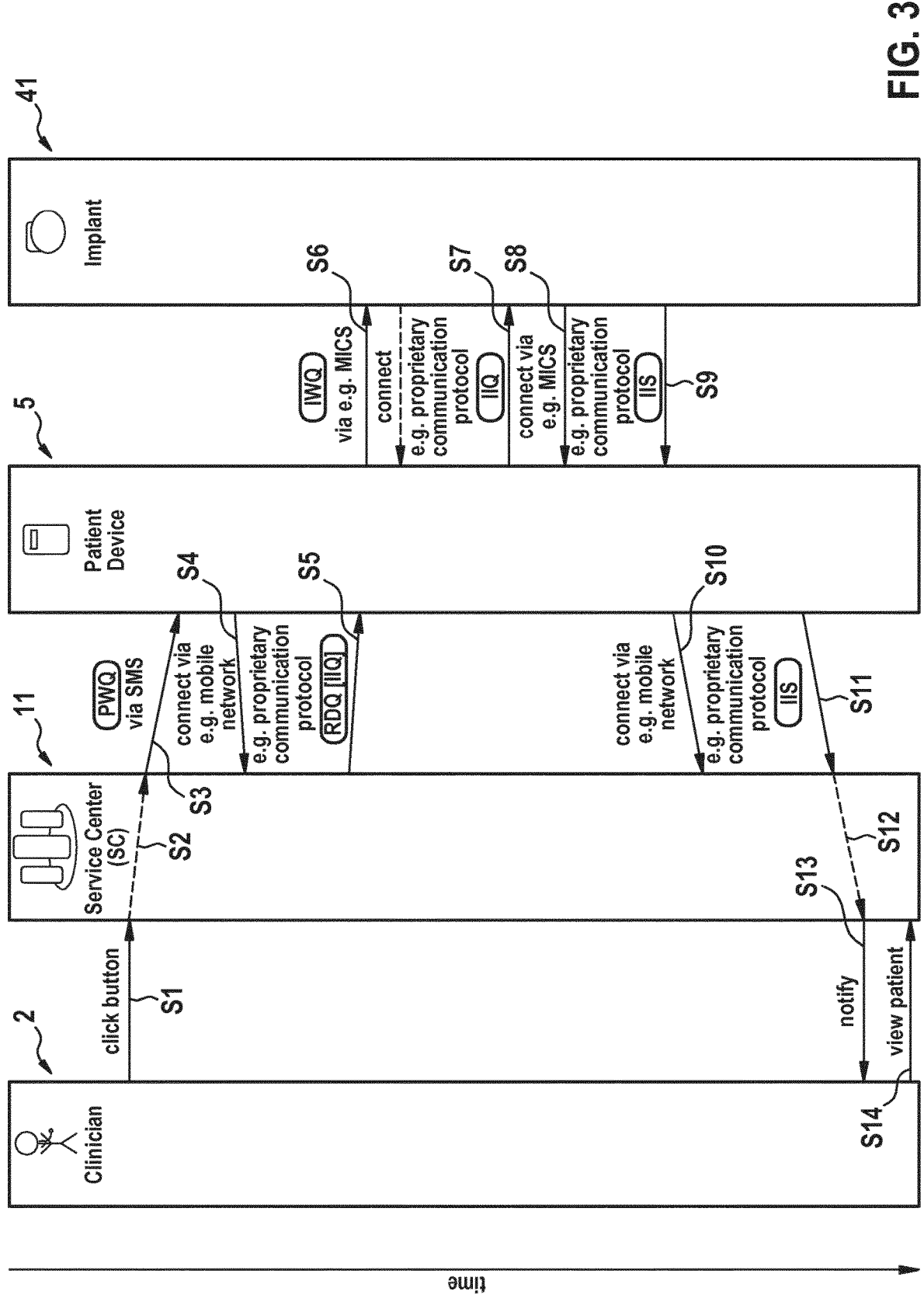
FIG. 3 shows a schematic drawing of a communication between a remote device in the shape of a service center, a patient device and an implantable medical device in the context of an interrogation.

Referring now to FIG. 3, a scheme for initiating a data transfer from an implantable medical device 41 shall be explained according to one exemplary embodiment. In this scheme, a remote device, to which data from an implantable medical device 41 (subsequently in short also denoted as implant) shall be transferred, is implemented by a service center 11, to which the data is forwarded and at which a user 1 via its user device 2 may view the data for examination and diagnosis.

Within the scheme of FIG. 3, different messages may, in one embodiment, be utilized for allowing an interrogation of an implant 41. Herein, a relay data request (RDQ) represents a request for the patient device 5 to relay data to the implant 41, a patient device wake-up request (PWQ) represents a request for the patient device 5 to connect to the service center 11, an implant wake-up request (IWQ) represents a request for the implant 41 to connect to the patient device 5, an implant interrogation request (IIQ) represents a request for the implant 41 to create an interrogation data set, and an implant interrogation response (IIS) represents a response from the implant 41 containing the interrogation data set.

Within the scheme as illustrated in FIG. 3, a user 1, e.g. a clinician, on the user device 2 may trigger an implant interrogation request, e.g. via a website of the service center 11, e.g. by performing a button click (step S1).

The service center 11 determines (e.g. using the serial number) the patient device 5 that is relaying messages for the implant 41 based on previously received messages (step S2). The service center 11 assembles a relay data request (RDQ) for the chosen patient device 5. The relay data request contains an implant interrogation request (IIQ), a priority value, an implant wake-up token and implant specific keys to be used by the patient device 5 in order to secure the implant wake-up request (IWQ). The implant wake-up token is different for each wake-up attempt.

The priority assigned to a relay data request herein serves two purposes. The actual value of the priority is used for prioritizing messages over other messages that have a lower priority value in queues along the way from the service center 11 to the implant 41. In addition, the priority value is used to potentially speed up the delivery of the request. For that purpose the range of possible priority values may be divided into several categories, e.g. "slow", "medium", "fast", "very fast" and "real time". For example, a priority value from the category "very fast" is chosen by the service center 11. A priority from this category will trigger a wake-up of both the patient device 5 and the implant 41.

In addition to prioritizing the request via the priority value/category, from this point on, the service center 11 will also process all messages received from the addressed patient device 5 and implant 41 with a higher priority than messages from patient devices 5 or implants 41 for which there is no ongoing interrogation.

In case of a priority of the category e.g. "very fast", the service center 11 sends a burst of patient device wake-up requests (PWQ) to the chosen patient device 5, e.g. via SMS or a wireless transmission (step S3). If the transport medium/technology does not support reliable reception feedback (e.g. as is the case with SMS), then sending more than one patient device wake-up requests may reduce the risk of a complete loss. The patient device wake-up requests serve to trigger the patient device 5 to connect to the service center 11 via a secure channel that is more reliable than the communication channel used for the wake-up, e.g. SMS. A patient device wake-up request contains a patient device wake-up token, which is different for each wake-up attempt.

As soon as a patient device 5 receives a patient device wake-up request with the expected patient device wake-up token, it connects to the service center 11, e.g. via mobile network (step S4). The connection uses a secure protocol (e.g. a proprietary protocol on top of TCP). The patient device wake-up token allows the patient device 5 to determine whether it has already responded to a given wake-up attempt. This makes sure that the patient device 5 connects only once for each relay data request.

Using the connection established in step S4, the service center 11 forwards the relay data request to the patient device 5 (step S5). If the priority as contained in the relay data request is of category "very fast", the patient device 5 is triggered to immediately terminate all current connections to the service center 11 (which may also serve for other purposes), skipping potentially slow operations like firmware updates, etc.

In addition, if the priority is "very fast", the patient device 5 immediately starts sending implant wake-up requests (implant wake-up request), e.g. via MICS/MedRadio/MEDS, containing the implant wake-up token, secured with the keys from the relay data request (step S6). As soon as the implant 41 receives an implant wake-up request that contains a valid implant wake-up token, a connection between the patient device 5 and implant 41 is established (e.g. via MICS/MedRadio/MEDS (optionally using a proprietary protocol) or via Bluetooth). The implant wake-up token allows the implant 41 to verify the authenticity of the wake-up request and the authorization of the user 1/service center 11/patient device 5 and to determine whether it has already responded to a given wake-up attempt. This makes sure that an implant 41 only responds once to each implant interrogation request.

During the connection established in step S6, the implant interrogation request contained in the relay data request is forwarded to the implant 41 (step S7). If the activity within the implant 41 triggered by the implant interrogation request would take longer than supported by the communication protocol, the connection is terminated. Otherwise it is kept open.

The implant 41 collects the data as defined in the implant interrogation request (IIQ) and, if the connection has not remained open during step S7, re-establishes a connection to the patient device 5 (step S8).

During the connection established in step S6 or re-established in step S8, the implant 41 forwards its implant interrogation response (IIS) to the patient device 5 (step S9).

On reception of the implant interrogation response, the patient device 5 terminates the connection and immediately initiates a connection to the service center 11, e.g. via a mobile network (step S10).

During the connection established in step S10, the patient device 5 forwards the implant interrogation response to the service center 11 (step S11).

The service center 11 calculates the new patient status based on the data contained in the implant interrogation response (step S12). This processing is expedited due to the prioritization of messages from the patient device 5 and implant 41 in step S2. From now on, messages received from the addressed patient device 5 or implant 41 will not be prioritized anymore (until the next request for interrogation).

The service center 11 notifies the user 1 about the reception of the implant interrogation response, e.g. via SMS and/or email (step S13).

The user 1 can now view the most up-to-date patient status (step S14).

The system and/or the method may offer an interrogation involving no or very limited patient interaction (as long as the patient's transmitter is close enough to the implant 41 and has network connectivity). Further, control of data capture may be improved. In addition, clinic workflows may be improved, and/or travel demands on patients to achieve desired care may be reduced. One or more of the advantages may come without requiring additional patient equipment outside of the normal system.

The features disclosed in regard with the system may also apply to the method and vice versa.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 User
2 User device (remote device)
4 Patient
41 Implantable medical device (IMD)
5 Patient device
6 Communication link (wired or wireless connection)
7 Communication link (wireless connection)
8 Hospital
9 Home
10 Communication link (wireless connection)
11 Service center (remote device)
S1-S14 Steps

The invention claimed is:

1. A method for initiating a data transfer from an implantable medical device, comprising:
generating a relay data request at a remote device, the relay data request containing an implant interrogation request representing a request for the implantable medical device to create an interrogation data set,
transferring the relay data request to a patient device,
establishing a communication link between the patient device and the implantable medical device to transmit said implant interrogation request to the implantable medical device,
transferring an implant interrogation response from the implantable medical device to the patient device, the implant interrogation response representing a response from the implantable medical device containing said interrogation data set, and
transferring the implant interrogation response from the patient device to the remote device,
wherein the patient device, upon receiving the implant interrogation response, establishes a communication connection to the remote device and forwards the implant interrogation response to the remote device.

2. The method according to claim 1, wherein said steps of transferring the relay data request, of establishing the communication link, of transferring the implant interrogation response and of transferring the implant interrogation response are performed by the remote device, the patient device and the implantable medical device without requiring any action by a user or a patient.

3. The method according to claim 1, wherein the remote device is a user device or a service center.

4. The method according to claim 1, wherein the relay data request, in addition to the implant interrogation request, contains at least one of a priority value, an implant wake-up token, and implant specific keys to be used by the patient device for communicating with the implantable medical device.

5. The method according to claim 1, wherein prior to said step of transferring the relay data request to the patient device, the remote device transmits at least one patient device wake-up request to the patient device, the at least one patient device wake-up request representing a request for the patient device to connect to the remote device.

6. The method according to claim 5, wherein, upon receiving said at least one patient device wake-up request, the patient device establishes a communication connection to the remote device, whereupon the remote device transfers the relay data request to the patient device using the communication connection.

7. The method according to claim 6, wherein the communication connection is established as a mobile network connection.

8. The method according to claim 1, wherein said step of establishing the communication link between the patient device and the implantable medical device includes: transmitting, by the patient device, at least one implant wake-up request to the implantable medical device.

9. The method according to claim 8, wherein the implantable medical device provides, at regular intervals, a time window for receiving the at least one implant wake-up request.

10. The method according to claim 8, wherein the communication link between the patient device and the implantable medical device is established by the implantable medical device when the at least one implant wake-up request is received by the implantable medical device.

11. The method according to claim 1, wherein the implantable medical device, upon receiving said implant interrogation request, collects data as defined in the implant interrogation request to generate said interrogation data set to be included in the implant interrogation response.

12. The method according to claim 1, wherein the implantable medical device re-establishes the communication link for transferring the implant interrogation response to the patient device if the communication link previously has been terminated.

13. The method according to claim 1, wherein said communication link is a MICS/MedRadio/MEDS, ISM or BLE link.

14. A system for initiating a data transfer from an implantable medical device, the system comprising a remote device, a patient device, and an implantable medical device, wherein:
the remote device is configured to generate a relay data request, the relay data request containing an implant interrogation request representing a request for the implantable medical device to create an interrogation data set,
the remote device is further configured to transfer the relay data request to the patient device,
the patient device and the implantable medical device are configured to cooperate to establish a communication link between the patient device and the implantable medical device to transmit said implant interrogation request to the implantable medical device,
the implantable medical device is configured to transfer an implant interrogation response to the patient device, the implant interrogation response representing a response from the implantable medical device containing said interrogation data set, and
the patient device is configured to transfer the implant interrogation response from the patient device to the remote device, and
the patient device, upon receiving the implant interrogation response, establishes a communication connection to the remote device and forwards the implant interrogation response to the remote device.

* * * * *